United States Patent [19]

Harless

[11] Patent Number: 5,595,982
[45] Date of Patent: Jan. 21, 1997

[54] EQUINE NUTRITIONAL SUPPLEMENT

[75] Inventor: Stanley J. Harless, Omaha, Nebr.

[73] Assignee: Harlmen Inc., Omaha, Nebr.

[21] Appl. No.: 220,512

[22] Filed: Mar. 31, 1994

[51] Int. Cl.$^6$ ........................ A61K 31/685; A61K 31/44; A61K 31/195; A61K 31/355
[52] U.S. Cl. ............................ 514/78; 514/345; 514/563; 514/355; 514/458; 514/702; 514/562; 514/729
[58] Field of Search .............................. 514/78, 345, 563, 514/355, 458, 562, 729; 424/702

[56] References Cited

U.S. PATENT DOCUMENTS

| | | | |
|---|---|---|---|
| 3,686,392 | 8/1972 | Hamada et al. | 424/16 |
| 4,743,591 | 5/1988 | Fukushima et al. | 514/30 |
| 5,082,662 | 1/1992 | Laurent et al. | 424/442 |
| 5,236,717 | 8/1993 | Vinci | 426/2 |
| 5,352,665 | 10/1994 | Awaya et al. | 514/15 |

*Primary Examiner*—Marianne M. Cintins
*Assistant Examiner*—William R. A. Jarvis
*Attorney, Agent, or Firm*—Larson & Taylor

[57] ABSTRACT

A nutritional supplement and a method of use therefor in equine are disclosed. The equine nutritional supplement alleviates various chronic or acute conditions in equine associated with hormonal imbalances. The equine nutritional supplement contains a lecithin, B vitamins, antioxidants such as vitamin E and/or selenium, and lipotropic agents such as inositol and/or methionine. The lecithin acts as a source of phospholipids and choline to improve and maintain body cell integrity. The equine nutritional supplement is particularly useful in extending the age of reproductive capability in equine.

7 Claims, No Drawings

EQUINE NUTRITIONAL SUPPLEMENT

FIELD OF THE INVENTION

The present invention is related to an equine nutritional supplement and, more particularly to a method of using an equine nutritional supplement to alleviate chronic or acute conditions in equine associated with physical aging, nutritional deficiencies, hormonal imbalances, and pathological changes of organs.

BACKGROUND OF THE INVENTION

Both human and animal cells have an external membrane referred to as a cell membrane or plasma membrane, which is comprised of two layers of phospholipid molecules. This double layer of phospholipid molecules is a lipid bilayer. The golgi apparatus, vesicles, including the lysosomes and peroxisomes, nucleus, and mitochondria are all within the cell and have their own lipid bilayers separating them from the cytoplasm of the cell.

As humans and animals age, cholesterol molecules replace phospholipid molecules and the cell membrane becomes more rigid and less functional. These already weakened cell membranes may be easily damaged due to free radicals produced by intracellular respiration. In addition, damage to receptors, which are an integral part of the lipid bilayer, may occur.

Vitamins and minerals are necessary for normal metabolic functioning of both humans and animals. Vitamins are either fat-soluble or water-soluble. The use of vitamin and mineral supplements to compensate for deficiencies thereof in humans due to age, poor eating habits or genetic defects is known in the art. By contrast, studies of the benefits of administering lecithin-based vitamin supplements to animals has been relatively limited, although animals are also known to suffer from various ailments as they increase in age.

In particular, equine are known to suffer from a number of conditions related to vitamin and minerals deficiencies due to poor quality forage or hay, chronic colic, chronic diarrhea, or anorexia resulting from dental disease. In addition, there may also be disturbances in absorption as the result of liver or biliary tract disease, hypothyroidism, anemia and other pathological conditions of the digestive system and related organs.

Numerous equine supplements are currently on the market. However, none of these supplements have been particularly effective in supplementing the diets of equine to extend the age of reproductive capability.

SUMMARY OF THE INVENTION

Thus, it is a purpose of the present invention to provide a nutritional supplement for alleviating various chronic or acute conditions in equine associated with physical aging, nutritional deficiencies, hormonal imbalances, and pathological changes of various organs. It is also a purpose of the present invention to provide a method of use for the equine nutritional supplement of the present invention.

In accordance with a preferred embodiment of the invention, an equine nutritional supplement for improving uterine tone in mares and sperm counts in stallions comprises vitamins and minerals in a lecithin base. Preferably, the equine nutritional supplement comprises a lecithin, B vitamins, antioxidants selected from the group consisting of vitamin E and selenium, and lipotropic agents selected from the group consisting of inositol and methionine. The equine nutritional supplement may further include choline, niacinamide, thiamine mononitrate, riboflavin, pyridoxine hydrochloride, pantothenic acid, zinc, biotin and dextrose.

It is therefore an object of the present invention to provide an equine nutritional supplement for improving and maintaining body cell integrity in equine and a method of use therefor.

It is another object of the present invention to provide an equine nutritional supplement for supplementing phospholipids in equine diets and a method of use therefor.

It is another object of the present invention to provide an equine nutritional supplement for improving uterine tone in older cycling breeding mares and improving libido and sperm count in older stallions, and a method of use therefor.

These and other objects of the present invention will become apparent from the detailed description to follow.

DESCRIPTION OF THE PREFERRED EMBODIMENTS

The equine nutritional supplement of the present invention comprises vitamins and minerals essential for body cell structure and cell metabolism. These vitamins and minerals are used by the body to both manufacture new cells and to maintain and repair existing normal or damaged cells. Specifically, the equine nutritional supplement of the present invention includes B vitamins which are needed in enzymatic reactions in the metabolic processes, methionine and/or inositol which provide lipotropic nutrients, and zinc. The equine nutritional supplement also includes antioxidants such as vitamin E and selenium. Vitamin E neutralizes free radicals formed during respiration in the mitochondria of the cell. Free radicals consist of $O_2^-$ anions. These anions damage the lipid bilayers of the cell. Selenium is a cofactor of glutathione peroxidase which destroys the peroxides generated during the interaction of the plasma membrane and free radical groups. Glutathione peroxidase levels in the plasma are directly related to dietary selenium.

The equine nutritional supplement further includes a lecithin base. Lecithin can be extracted from several sources including egg yolks and soybeans. Thus, lecithin is comprised of many different types and mixtures of phospholipids and glycolipids depending upon the source.

Lecithin provides three functions after ingestion. First, lecithin acts an emulsifying agent to promote the rapid breakdown of food particles so digestive enzymes can more readily break down the substrates. This promotes digestion and absorption, which enhances the utilization of the fat soluble and water soluble vitamins.

Second, soybean lecithin contains the exact same phospholipids found in the cell membrane (plasma membrane) of mammals. These phospholipids are phosphatidylcholine, phosphatidylethanolamine, phosphatidylinositol, and phosphatidylserine, which form the major phospholipids of the plasma membrane of the cell. Therefore, loading the diet with a phospholipid rich supplement promotes cellular repair and maintenance. In addition, lipid soluble chemicals move freely across the blood brain barrier. This is significant because unless this barrier is voided by pathological changes or trauma, non-lipid soluble chemicals, other than water, do not enter the brain. Phospholipids can carry both water soluble and fat soluble chemicals across this barrier. This is possible since phospholipids are amphipathic, having both hydrophilic and hydrophobic properties.

Thirdly, lecithin contains diphosphatidylcholine, which is comprised of two molecules of choline and one molecule of glycerol. The body must have choline for the synthesis of acetylcholine, the major neurotransmitter in the central and peripheral nervous system. Choline, by itself, is subject to degradation by stomach and intestinal bacteria, which may render most of the choline useless to the body and, further cause a pungent odor in fecal matter. However, supplementation with disphosphatidylcholine conserves the choline because it is absorbed as a phospholipid. Since the brain and peripheral nervous system is so dependent upon the neurotransmitter acetylcholine, supplementing the equine diet with a lecithin containing large amounts of diphosphatidylcholine is an efficient method of choline loading, i.e., of supplementing choline in the body in a form that is not degraded by bacteria in the intestine, and can be absorbed by the cells.

Choline is also the rate limiting precursor of acetylcholine. The thalamus and the hypothalamus of the brain are predominantly cholinergic, i.e., dependent on acetylcholine as the neuro-transmitter, and produce small peptides including TSH and LH releasing factors, as well as control the function of the pituitary gland. The pituitary gland, in turn, produces hormones that affect the thyroid gland, adrenal gland, testes, and ovaries. In addition the pituitary produces somatotropin, and vasopressin. The general health and reproduction in equine is related to the individual and combined hormonal effects on all of the organ systems of the body. Thyroid levels in particular have a very significant effect on the reproductive systems of any animal and are necessary for normal functioning of all cells.

The equine nutritional supplement of the present invention comprises the following compounds: a lecithin, B vitamins, antioxidants selected from the group consisting of vitamin E and selenium, and lipotropic agents selected from the group consisting of inositol and methionine. The equine nutritional supplement may also include biotin, zinc, choline, niacinamide, thiamine mono nitrate, riboflavin, pyridoxine HCL, pantothenic acid and dextrose. In a preferred embodiment of the invention, the equine nutritional supplement comprises the following compounds shown in weight percentages:

| Compound | % by Weight |
| --- | --- |
| Lecithin | 36–40 |
| DL Methionine | 4.8–5.1 |
| Choline | 1.2–1.3 |
| Inositol | 1.2–1.3 |
| Niacinamide | .39–.41 |
| Thiamine Mono nitrate | .12–.16 |
| Riboflavin | .11–.12 |
| Pyridoxine HCL | .068–.075 |
| Pantothenic acid | .065–.075 |
| Vitamin B-12 600 mg (concentration of stock vitamin supplement) | .350–.500 |
| Zinc sulfate 36% (36% zinc as zinc sulfate, 64% as zinc in other non-absorbable states) | 2.65–2.80 |
| Vitamin E | .38–.45 |
| Selenium 2% (9.072 g/lb stock solution) | .18–.210 |
| Biotin 1% Food Grade | .650–.690 |
| Dextrose | 45–55 |

In a most preferred embodiment of the invention, the equine supplement comprises the following:

| Compound | % by Weight |
| --- | --- |
| Lecithin | 36.7 |
| DL Methionine | 4.90 |
| Choline | 1.23 |
| Inositol | 1.22 |
| Niacinamide | .39 |
| Thiamine Mono nitrate | .12 |
| Riboflavin | .11 |
| Pyridoxine HCL | .072 |
| Pantothenic acid | .070 |
| Vitamin B-12 600 mg/lb | .400 |
| Zinc sulfate 36% | 2.77 |
| Vitamin E | .40 |
| Selenium 2% Intermed | .200 |
| Biotin 1% FG | .662 |
| Dextrose | 51.15 |

It is to be understood that the equine nutritional supplement of the present invention is not limited to the specific compounds and concentrations noted above. The equine nutritional supplement may be administered in various forms such as liquid or tablet. Preferably, however, the equine nutritional supplement is in a powder form which is mixed into food, such as by pouring it over grain. The equine nutritional supplement may also be formulated with a flavored base to improve its taste.

The quantity of the formulation administered to an equine is dependent on various factors such as general health, weight, age, state of nutrition, and type and severity of the ailment. For example, a single standard dosage of the preferred formulation described above is approximately 35–40 grams. An equine having a severe ailment, however, could require two or more of these standard dosages.

In some cases, administering the equine nutritional supplement may only be necessary for or a short time period. For treatment of breeding mares, for example, treatment may only be necessary to improve uterine tone just before breeding, during pregnancy and during lactation. Similarly, when administered to older stallions to improve sperm count and libido, the equine nutritional supplement may only be required during the breeding season. However, in the case of chronic ailments such as hives, chronic colic or soreness, continued treatment may be necessary even after symptoms disappear.

As demonstrated in Examples 1–6, the effects of the equine nutritional supplement were evaluated through both observations and clinically by means of blood tests. In particular, since the thyroid gland is controlled by the brain and influenced by the supply of neuro-transmitters, changing thyroid hormone levels can indicate positive therapeutic changes. Thyroid hormones are measured by a number of methods including radioimmunoassay. The thyroid hormone containing 4 iodine radicals is referred to as $T_4$. Intracellular enzymes remove one iodine radical and the thyroid hormone is then referred to as $T_3$. $T_3$ is the form that the body can use on a cellular level. If intracellular enzymes are not present in sufficient quantities, then the cells cannot convert $T_4$ to $T_3$. $T_4$ and $T_3$ levels can be measured readily and are useful as indicators of therapeutic improvement.

Although the invention has been described in considerable detail with respect to preferred embodiments thereof, variations and modifications will be apparent to those skilled in the art without departing from the spirit and scope of the invention as set forth in the claims.

EXAMPLE 1

The equine nutritional supplement was administered to a nine-year old paint mare having the primary problems of an atonic uterus, transient estrous cycle, and inability to breed due to lack of adequate follicular formation and ovulation. Secondary problems included grade II intermittent lameness bilaterally on front feet, above-average weight, changes in disposition and recurrent urticaria. Initial $T_3T_4$ blood levels were as follows: $T^3=0$ ng/dl; $T_4=4$ ng/dl. After three days of receiving the equine nutritional supplement, rectal palpation was performed and revealed a dramatic increase in uterine tone. After one week of treatment with the equine nutritional supplement, the mare had a normal estrous cycle and was successful bred. 15 days post-breeding, the mare was examined by ultrasound and diagnosed with a twin pregnancy. One embryo was pinched and ultrasound 10 days later showed resorption of the other embryo. The mare lost weight and both her hair coat and lameness improved. She was put back in training as a show horse. $T_3T_4$ blood levels after 3 months of treatement with the supplement were as follows: $T_3=29$ ng/dl; $T_4=9$ ng/dl. While on the equine nutritional supplement, the mare did not have any hives; when taken off the equine nutritional supplement, the hives would recur in about a week.

EXAMPLE 2

The equine nutritional supplement was administered to a nineteen year old American Standard Bred gelding having the primary problems of poor condition, long hair and low body weight. A secondary problem was a cranky attitude. Initial $T_3T_4$ blood levels were as follows: $T_3=0$ ng/dl; $T_4=14$ ng/dl. After ten days of receiving the equine nutritional supplement, there was a dramatic change in weight and hair coat and improvement in attitude. $T_3T_4$ blood levels after 30 days of treatment with the supplement were as follows: $T_3=12$ ng/dl; $T_4=80$ ng/dl.

EXAMPLE 3

The equine nutritional supplement was administered to a ten year old Arabian gelding. The gelding had suffered from a case of acute laminitis, approximately three years prior, which was unsuccessfully treated resulting in severe rotation of the third phalanx and chronic lameness. Hoof walls were also deformed. Blood samples taken before and after one week of receiving the equine nutritional supplement showed a significant improvement in the gelding's health. The gelding's ability to walk, trot and canter continued to improve during four months of treatment with the equine nutritional supplement.

EXAMPLE 4

The equine nutritional supplement was administered to a five year old quarter horse mare having a primary problem of agalactia. After one day of treatments with oxytocin and receiving the equine nutritional supplement, the mare's foal was more comfortable and relaxed after nursing. An IgG blood test on the foal (used to determine the state of the foal's immune system) was within normal limits at 24 hours of life. After three days of treating the mare, the foal's flanks were full and he was resting normally. The foal was weaned after five months, grew normally, and was actually very fleshy and one of the bigger foals in a group of twenty.

The equine nutritional supplement was administered to many other poor milking mares with similar successful results.

EXAMPLE 5

The equine nutritional supplement was administered to a nine year old quarter horse gelding having a primary problem of acute myositis. Secondary problems included chronic colic and chronic soreness in the thorax, shoulders and distal neck. A blood chemistry screen revealed an elevation in liver enzymes and LDH. Treatment of the gelding included the following: chiropractic adjustment of thoracic vertebrae and $C_7$, balancing of feet and elevation of heels and administering of the equine nutritional supplement. The gelding's physical condition improved immediately with no sign of tie-up or colic for two months. The gelding moved normally and was shown at a horse show. When equine nutritional supplement treatment was discontinued, similar symptoms returned. However, once the equine nutritional supplement was again administered, the gelding's condition again improved.

I claim:

1. A method for alleviating chronic or acute conditions associated with hormonal imbalances in an equine, the method comprising administering a nutritional supplement to said equine, the nutritional supplement comprising lecithin, B vitamins, antioxidants selected from the group consisting of vitamin E and selenium, and lipotropic agents selected from the group consisting of inositol and methionine.

2. The method according to claim 1 wherein said nutritional supplement further comprises biotin, zinc, choline, niacinamide, thiamine mono nitrate, riboflavin, pyridoxine HCL, pantothenic acid and dextrose.

3. The method according to claim 2 wherein the supplement comprises the following compounds in percentage by weight: 36–40% lecithin, 4.8–5.1% DL-methionine, 1.2–1.3% choline, 1.2–1.3% inositol, 0.39–0.41% niacinamide, 0.12–0.16% thiamine mononitrate, 0.11–0.12% riboflavin, 0.068–0.075% pyridoxine hydrochloride, 0.065–0.075% pantothenic acid, 0.35–0.50% vitamin B-12 600 mg/lb, 2.65–2.80% zinc sulfate 36%, 0.38–0.45% vitamin E, 0.18–0.21% selenium 2%, 0.65–0.69% biotin 1% and 45–55% dextrose.

4. An equine nutritional supplement comprising lecithin, B vitamins, antioxidants selected from the group consisting of vitamin E and selenium, and lipotropic agents selected from the group consisting of inositol and methionine, said nutritional supplement comprising at least 36 percent by weight of said lecithin.

5. The nutritional supplement according to claim 4 further comprising biotin, zinc, choline, niacinamide, thiamine mono nitrate, riboflavin, pyridoxine HCL, pantothenic acid and dextrose.

6. The nutritional supplement according to claim 4 comprising the following compounds in percentage by weight: 36–40% lecithin, 4.8–5.1% DL-methionine, 1.2–1.3% choline, 1.2–1.3% inositol, 0.39–0.41% niacinamide, 0.12–0.16% thiamine mononitrate, 0.11–0.12% riboflavin, 0.068–0.075% pyridoxine hydrochloride, 0.065–0.075% pantothenic acid, 0.35–0.50% vitamin B-12 600 mg/lb, 2.65–2.80% zinc sulfate 36%, 0.38–0.45% vitamin E, 0.18–0.21% selenium 2%, 0.65–0.69% biotin 1%, and 45–55% dextrose.

7. The equine nutritional supplement according to claim 4 wherein said lecithin comprises soybean lecithin.

* * * * *